United States Patent
Bourdeaux et al.

(10) Patent No.: US 8,489,431 B2
(45) Date of Patent: Jul. 16, 2013

(54) SYSTEM AND METHOD OF REMOTE REPORTING OF RADIATION DOSE USAGE IN IMAGE ACQUISITION

(75) Inventors: Guillaume Bourdeaux, Paris (FR); Jennifer Esposito, Whitefish Bay, WI (US); David Ysseldyke, Delafield, WI (US); Barry Belanger, Chenequa, WI (US)

(73) Assignee: General Electric Company, Schenectady, NY (US)

( * ) Notice: Subject to any disclaimer, the term of this patent is extended or adjusted under 35 U.S.C. 154(b) by 597 days.

(21) Appl. No.: 12/408,394

(22) Filed: Mar. 20, 2009

(65) Prior Publication Data

US 2010/0239069 A1    Sep. 23, 2010

(51) Int. Cl.
*G06Q 10/00* (2006.01)

(52) U.S. Cl.
USPC .................................................. 705/3; 705/2

(58) Field of Classification Search
USPC ......................................................... 705/2–3
See application file for complete search history.

(56) References Cited

U.S. PATENT DOCUMENTS

| | | | |
|---|---|---|---|
| 6,095,973 A | 8/2000 | Joseph | |
| 6,228,027 B1 | 5/2001 | Joseph | |
| 6,347,329 B1 * | 2/2002 | Evans | 709/202 |
| 7,539,284 B2 * | 5/2009 | Besson | 378/62 |
| 8,130,905 B1 * | 3/2012 | Nelms | 378/65 |
| 2006/0274145 A1 * | 12/2006 | Reiner | 348/62 |
| 2007/0106752 A1 | 5/2007 | Moore | |
| 2008/0103834 A1 * | 5/2008 | Reiner | 705/3 |
| 2010/0310048 A1 * | 12/2010 | Hoornaert | 378/97 |

FOREIGN PATENT DOCUMENTS

WO    2007080522    7/2007

OTHER PUBLICATIONS

US Food and Drug Administration; "Recording Information in the Patient's Medical Record that Identifies the Potential for Serious X-ray Induced Skin Injuries"; Sep. 15, 1995 (updated Apr. 25, 1996); www.fda.gov.*
"Frequently Asked Questions on Cabinet X-Ray Systems," http://www.fda.gov/cdrh/radhealth/products/cabinetxrayfaq.html < (Oct. 24, 2008).
"What are the Radiation Risks from CT?" http://www.fda.gov/cdrh/ct/risks.html < (Aug. 6, 2008).

(Continued)

*Primary Examiner* — Michael Fuelling
(74) *Attorney, Agent, or Firm* — Fletcher Yoder, P.C.

(57) ABSTRACT

A system and method to manage direction of an ionizing radiation toward an exposed subject is provided. The system can perform receiving a request from a customer to establish an internet connection to communicate between a remote office and the system directing the ionizing radiation toward the exposed subject; automatically communicating a status information and individual dose data associated with an event where direction of ionizing radiation that exceeds a threshold; automatically creating and communicating a report via the internet connection to the customer. The report can include an indication of the event where direction of ionizing radiation exceeds the threshold and a comparison of the individual radiation dose data and an individual status operation of system at time of the event relative to a benchmark defined by radiation dose data and status information acquired from a population of other systems.

15 Claims, 9 Drawing Sheets

OTHER PUBLICATIONS

"Radiation Quantities and Units," http://www.fda.gov/cdrh/ct/rqu.html < (Apr. 17, 2002).

Food and Drug Administration, "Avoidance of Serious X-Ray-Induced Skin Injuries to Patients During Fluoroscopically-Guided Procedures," pp. 1-6, 1994.

Shope, "Radiation-Induced Skin Injuries from Fluoroscopy," http://www.fda.gov/cdrh/rsnail.html < (Aug. 5, 1997).

"FDA Public Health Advisory: Avoidance of Serious X-Ray-Induced Skin Injuries to Patients Durning Fluoroscopically-Guided Procedures," http://www.fda.gov/cdrh/fluor.html < (May 2, 1996).

"Recording Information in the Patient's Medical Record that Identifies the Potential for Serious X-Ray-Induced Skin Injuries," http://www.fda.gov/cdrh/xrayinj.html < (Apr. 15, 1996).

* cited by examiner

| | | DURATION (MIN) | DURATION (%) | TOTAL DOSE (ESAK, mGy) | TOTAL DOSE (ESAK, %) | DAP (mGy, cm²) | DAP (%) |
|---|---|---|---|---|---|---|---|
| AORTA | FLUORO | 1276 | 77.46% | 48205 | 42.41% | 509724 | 42.83% |
| | DSA | 121 | 7.36% | 46654 | 41.04% | 511770 | 43.00% |
| | BOLUSCHASE | 78 | 4.76% | 777 | 0.68% | 16039 | 1.35% |
| | CHASE | 8 | 0.47% | 662 | 0.58% | 6697 | 0.56% |
| | 3D | 2 | 0.10% | 396 | 0.35% | 4085 | 0.34% |
| CORONARIES | CARDIAC | 5 | 0.31% | 3971 | 3.49% | 21771 | 1.83% |
| | FLUORO | 29 | 1.77% | 2685 | 2.36% | 14761 | 1.24% |
| AORTA-ARCH | DSA | 6 | 0.35% | 2937 | 2.58% | 41906 | 3.52% |
| | FLUORO | 40 | 2.40% | 1754 | 1.54% | 21229 | 1.78% |
| | BOLUSCHASE | 11 | 0.64% | 190 | 0.17% | 4113 | 0.35% |
| | CHASE | 0 | 0.02% | 79 | 0.07% | 654 | 0.05% |
| FEMORAL | FLUORO | 37 | 2.24% | 1293 | 1.14% | 10595 | 0.89% |
| | DSA | 5 | 0.32% | 977 | 0.86% | 5731 | 0.48% |
| CUSTOM2 | CARDIAC | 1 | 0.04% | 1029 | 0.91% | 3856 | 0.32% |
| | FLUORO | 3 | 0.21% | 233 | 0.20% | 1138 | 0.10% |
| CUSTOM1 | CARDIAC | 1 | 0.04% | 551 | 0.48% | 3909 | 0.33% |
| | FLUORO | 2 | 0.13% | 222 | 0.20% | 1557 | 0.13% |
| FOOT | FLUORO | 10 | 0.61% | 264 | 0.23% | 3851 | 0.32% |
| | DSA | 1 | 0.09% | 238 | 0.21% | 2413 | 0.20% |
| | BOLUSCHASE | 2 | 0.14% | 34 | 0.03% | 756 | 0.06% |
| UNSUB DSA | DSA | 0 | 0.03% | 164 | 0.14% | 667 | 0.06% |
| | FLUORO | 0 | 0.02% | 35 | 0.03% | 206 | 0.02% |
| LOWER LEG | DSA | 0 | 0.01% | 97 | 0.09% | 392 | 0.03% |
| | BOLUSCHASE | 5 | 0.28% | 88 | 0.08% | 1135 | 0.10% |
| | FLUORO | 1 | 0.05% | 11 | 0.01% | 141 | 0.01% |
| CAROTIDS | FLUORO | 2 | 0.14% | 72 | 0.06% | 647 | 0.05% |
| | DSA | 0 | 0.02% | 50 | 0.04% | 429 | 0.04% |
| TOTAL | | 1647 | 100% | 113668 | 100% | 1190172 | 100% |

SYSTEM AND METHOD OF REMOTE REPORTING OF RADIATION DOSE USAGE IN IMAGE ACQUISITION

BACKGROUND

The subject matter of this application generally relates to ionizing radiation (e.g., x-rays), and more specifically to a system and method to manage direction of ionizing radiation dose toward an exposed subject.

Employment of the use of ionizing radiation (e.g., x-ray) is well known in the therapy or image acquisition of an exposed subject. Fields of application of ionizing radiation is common in the medical field (e.g., fluoroscopic, computed tomography (CT), x-ray, ablation of tissue, etc.) and security screening (e.g., airport baggage inspection). For example, radiological image acquisition generally includes directing a stream of ionizing radiation at the exposed subject, and measuring the attenuation of the ionizing radiation passing therethrough.

One concern with use of ionizing radiation include an increased likelihood of harm or injury associated with radiation-induced injury to the tissue of the exposed subject. These deterministic risks can include skin reddening, rashes, burns, or hair loss. In fact, use of ionizing radiation is well-known in chemo-therapy or the ablation of diseased tissue. A variable that affects a likelihood of causing radiation-induced injury to tissue of an exposed subject includes a dose of radiation absorbed by the exposed subject. Variables that affect a dose of radiation absorbed by the exposed subject include a rate of delivery of radiation to the exposed subject, a time of exposure of radiation to the exposed subject, a fraction of radiation absorbed by the exposed subject, age or other characteristics of the exposed subject, and a location of exposure of radiation to the exposed subject. Another concern with use of ionizing radiation includes an increased likelihood of causing stochastic effects (e.g., radiation-induced cancers) to the exposed subject.

BRIEF DESCRIPTION OF CLAIMED SUBJECT MATTER

In view of the above concerns associated with use of ionizing radiation, there is a need for improved access to data or increased knowledge to manage direction of radiation dose toward the exposed subject (e.g., patient) for different applications (e.g., fluoroscopic imaging, x-ray imaging, CT imaging of various exposed areas (e.g., chest, arms, legs, etc.) of an exposed subject). This improved access to data can benefit the establishment of standard operating procedures and protocols in the use of ionizing radiation to perform various tasks, as well as benefit the measurement and evaluation of an impact of each procedure's protocol in the likelihood for deterministic or stochastic effects associated with exposure to ionizing radiation relative to the characteristics of exposed subjects. The above-described needs and benefits are addressed by the embodiments of the subject matter described herein.

One embodiment of the subject matter includes a method to manage direction of an ionizing radiation toward an exposed subject, comprising the steps of receiving a request from a customer to establish an internet connection to communicate between a remote office and the system directing the ionizing radiation toward the exposed subject; automatically communicating a status information and individual dose data associated with an event where direction of ionizing radiation that exceeds a threshold; automatically creating and communicating a report via the internet connection to the customer, the report including an indication of the event where direction of ionizing radiation exceeds the threshold and a comparison of the individual radiation dose data and an individual status operation of system at time of the event relative to a benchmark defined by radiation dose data and status information acquired from a population of other systems that direct ionizing radiation and communicate data to the remote office.

Another embodiment of the subject matter includes A computer readable medium including a plurality of program instructions for execution by a processor to perform the steps of: receiving a request from a customer to establish an internet connection to communicate between a remote office and the system directing the ionizing radiation toward the exposed subject; automatically communicating a status information and individual dose data associated with an event where direction of ionizing radiation that exceeds a threshold; automatically creating and communicating a report via the internet connection to the customer, the report including an indication of the event where direction of ionizing radiation exceeds the threshold and a comparison of the individual radiation dose data and an individual status operation of system at time of the event relative to a benchmark defined by radiation dose data and status information acquired from a population of other systems that direct ionizing radiation and communicate data to the remote office.

Systems and methods of varying scope are described herein. In addition to the aspects and advantages described in this summary, further aspects and advantages will become apparent by reference to the drawings and with reference to the detailed description that follows.

DETAILED DESCRIPTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
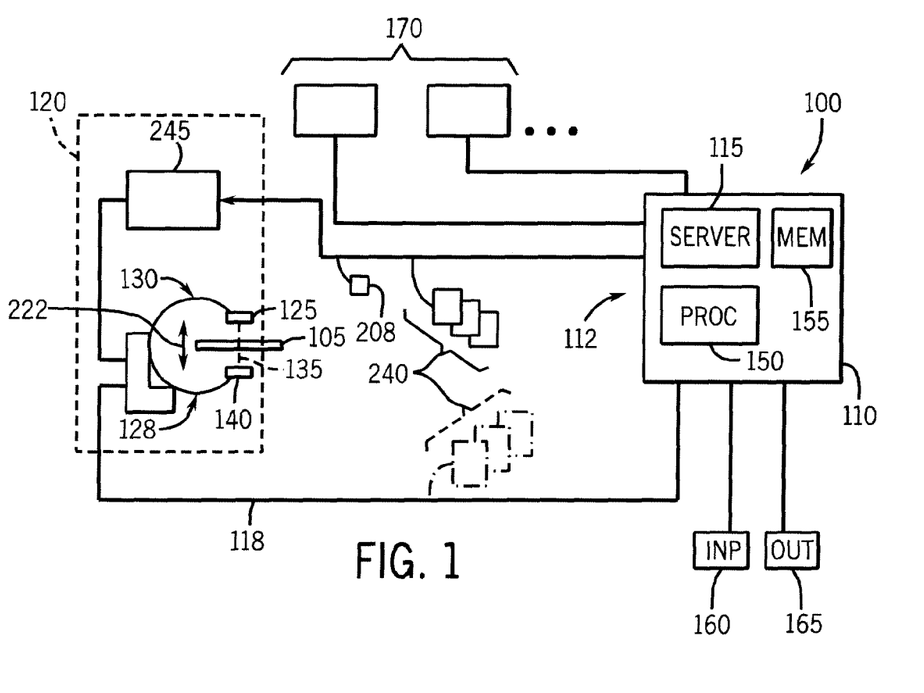
FIG. 1 shows a schematic diagram of an embodiment of a system to manage direction or delivery of ionizing radiation dose toward an exposed subject.

FIG. 1 illustrates one embodiment of a management system 100 to remotely monitor and report usage of radiation dose in acquisition of medical images or other protocol involving direction of ionizing radiation dose toward an exposed subject 105. The system 100 can generally include a controller 110 located at a remote workstation or office 112 having a server 115 in communication via an internet or broadband or wireless connection 118 with an ionizing radiation generating or emitting system or device 120. Remote office 112 as used herein generally refers to a location off-site of the facility or entity or address of the location of the customer. Yet, an embodiment of the system 100 can include one or more portions located at the customer and is not limiting on the subject matter.

One example of the ionizing radiation system 120 includes a radiation source 125 (e.g., x-ray tube assembly to generate x-rays) supported on a gantry 128 of a radiological imaging system 130. Examples of the radiological imaging system 130 generally include an x-ray machine, computed tomography (CT), a fluoroscopic imaging system, etc. having the radiation source 125 projecting a beam of ionizing radiation (e.g., x-rays) 135 through the exposed subject 105 to be received at a detector 140 in a conventional manner. The ionizing radiation can be attenuated with passing through exposed subject 105, until impinging upon the detector 140. The detector 140 can translate the attenuation of ionizing radiation to generate the image or image frames illustrative of a region of interest of the exposed subject 105. An example of the radiological imaging system 130 can also include a software product or package operable to combine a series of acquired images to create the reconstructed three-dimensional image. An example of the software product is INNOVA® 3D as manufactured by GENERAL ELECTRIC®. The software product can also operable to measure a volume, a diameter, and a general morphology of a vessel (e.g., vein, artery, etc.) or other anatomical structures.

An embodiment of the system 100 can generally include the controller 110 in communication via the internet connection 118 to acquire data from the radiation source 125 or radiological imaging system 130. One embodiment of the system 100 includes a software product such as INSITE® as manufactured by GENERAL ELECTRIC COMPANY® or INNERVISION® PLUS as manufactured by TOSHIBA® to establish the connection 118 between the ionizing radiation system 130 and the controller 100 at the remote office 112.

Although the controller 110 can be described at the remote office 112, it should be understood that the controller 110 can otherwise be located integrated with or adjacent to the system 130 directing of ionizing radiation dose toward an exposed subject 105.

An embodiment of the controller 110 can be generally configured to process and analyze the acquired data (e.g. status information). An embodiment of the controller 110 generally includes a processor 150 in communication with a memory 155. The memory 155 can generally include a computer readable storage medium operable to receive and store computer readable program instructions for execution by the processor 150. The memory 155 is also generally operable to store acquired data communicated by the radiation source 125 or imaging system 130 or from other sources 170 (e.g., MRI systems, PET imaging system, picture archival system (PACS), etc.). The type of memory 155 can include disk storage, tape drive, random access memory (RAM), read-only memory (ROM), flash memory, compact disk (CD), digital versatile disks (DVDs), magnetic cassettes, magnetic tape, magnetic disk storage, or any other medium operable to be used to store computer readable instructions.

The controller 110 is also in communication with an input device 175 and an output device 180. An embodiment of the input 175 can include a keyboard, user interface with touch-screen capability, mouse device, etc. operable to receive instructions or data from a user of the system 100. An embodiment of the output device 180 can include a monitor, audible or visual alarms, etc. operable to illustrate output from the system 100 to the user.

Figure 2:
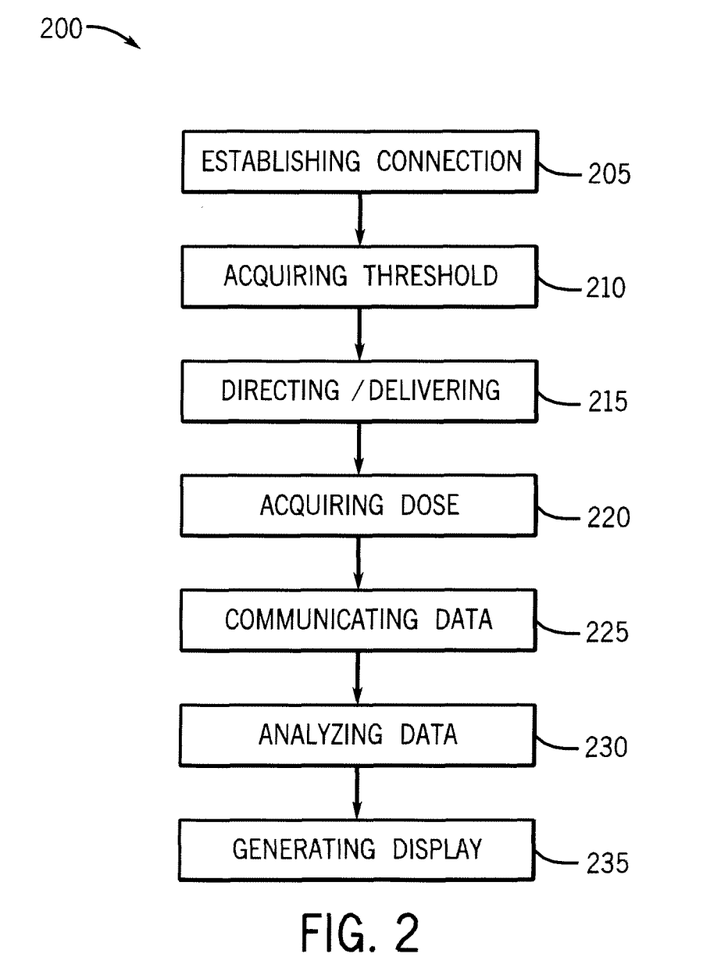
FIG. 2 shows a schematic diagram of a method of operating the system to manage direction or delivery of ionizing radiation toward an exposed subject.

Having described the general construction of the system 100, the following is a description of a method 200 of operating the system 100 in management of delivery or direction of ionizing radiation to the exposed subject 105. It should be understood that the foregoing sequence of acts or steps comprising the method 200 can vary, that the method 200 may not include each every act or step in the following description, and the method 200 can include additional acts or steps not disclosed in the following description. One or more of the following acts or steps comprising the method 200 can be represented as computer-readable programmable instructions for storage in the memory or on a portable computer readable medium 155 and for execution by the processor 150 of the controller 110.

Assume for sake of example that an exposed subject 105 is a patient and the ionizing radiation system 130 includes a computed tomography (CT) imaging system operable to perform image acquisition.

Step 205 includes receiving a request 208 to establish a broadband connection 118 (e.g., internet) between the radiological imaging system 130 and the remote workstation 112 (e.g., remote office). The format of the request 208 can be an electronic message (e.g., email) over the internet, electronic communication over the internet or broadband connection 118, electronic communication via a webpage, etc. An embodiment of step 205 can include establishing a connection 118 via INSITE® product as manufactured by GENERAL ELECTRIC COMPANY®. Step 210 includes acquiring an upper threshold of radiation dose to direct from the radiological imaging system to the patient. One embodiment of acquiring the upper threshold can be from a user of the radiological imaging system 130 and can be communicated via the broadband connection 118. Yet, the mode of communicating (e.g., telephone, electronic mail, etc.) the upper threshold can vary. Step 215 includes directing or delivering the beam or stream of ionizing radiation 135 through the exposed subject 105.

Step 215 includes data associated with performing image acquisition on the patient 105. An embodiment of step 215 includes acquiring a protocol or task 216 (See FIG. 5) of image acquisition to perform on the patient 105, a location 218 (e.g., anatomical region) of image acquisition on the patient 105, etc.

Step 220 includes acquiring a dose or dose rate of radiation (e.g., absorbed dose in Gray (Gy), cumulative air kerma with regards to fixed reference position with regards to the interventional reference point at a fixed distance from the isocenter of the imaging system 130, equivalent dose in sievert (Sv), effective dose relative to a tissue weighting factor, Computed Tomography Dose Index (CTDI), weighted CTDI, volume CTDI, multiple scan average dose (MSAD), dose length product (DLP), etc.) directed by the individual imaging system 130 in acquisition of images of the patient 105, a patient position relative to the imaging system 130 or radiation source 125, a distance between the radiation source 125 (e.g., x-ray tube assembly focal spot where the electron beam hits the anode target) to the scintillator of the flat panel detector) (also referred to as source to image distance (SID)) 222, a comparison of the directed dose relative to the acquired upper dose threshold, a measure of radiation dose directed per SID, a cumulative dose directed to the patient for each SID or SID grouping, details of the status information (e.g., acquisition mode, positioning of radiation source 125 and/or scanner/detector 140 in relation in time to direct radiation dose or cumulative dose, frame rate, auto exposure preference, detail level of image data, total number of runs or scans, total scan time or duration of image acquisition, details associated with calibration (e.g., calibration date, etc.) of the imaging system 130, and total radiation dose directed to the patient 105).

Step 220 can also include acquiring data (e.g., calibration status, dates, etc.) associated with calibration of the individual imaging system 130. Step 220 can also include acquiring status information associated with operation of the imaging system 130, including error messages, alerts, and other parameters, relative to manufacturer specifications.

Step 225 includes communicating a portion or all of the acquired data described under step 220 to the remote office or station 112. One embodiment of step 225 includes communicating the portion or all of the acquired data via the broadband connection 118. Yet, the acquired data can be communication over other modes of communication (e.g., wireless, telephone, broadband, attached files sent via electronic mail, etc. or combination). Step 225 can be performed in general real-time basis, on a batch basis, or periodically as predetermined by either the user of the imaging system 130 or the remote office 112.

One embodiment of step 225 can include communication of a portion or all of the acquired data described in step 220 with respect to an individual imaging system 130 in response to detecting an exceedance of the dose threshold (e.g., cumulative dose threshold, etc.).

Step 230 includes analyzing the acquired data from the individual imaging system 130. One embodiment of step 230 includes compared one or more types or parameters represented by the acquired data relative to a threshold. One embodiment of the threshold can be determined relative to a predetermined value (e.g., regulation) for radiation dose directed to the exposed subject 105. Another embodiment of step 230 can include grouping or categorizing the acquired data or characteristics of the individual imaging system 130 for comparison to acquired data from one or more other similar imaging systems 170 or similar procedures/tasks/protocol of image acquisition or combination thereof.

Step 235 includes generating a report 240 illustrative of the above-described analyses performed on the acquired data for illustration to the user at a display 245 of a user workstation or of the individual imaging system 130. One embodiment of the above-described report 240 can include graphic representations of the acquired data in step 220 in comparison relative to itself or relative to one or more atypical imaging systems in the population of imaging systems 170 that the remote office or station 112 acquires data from.

Figure 3:
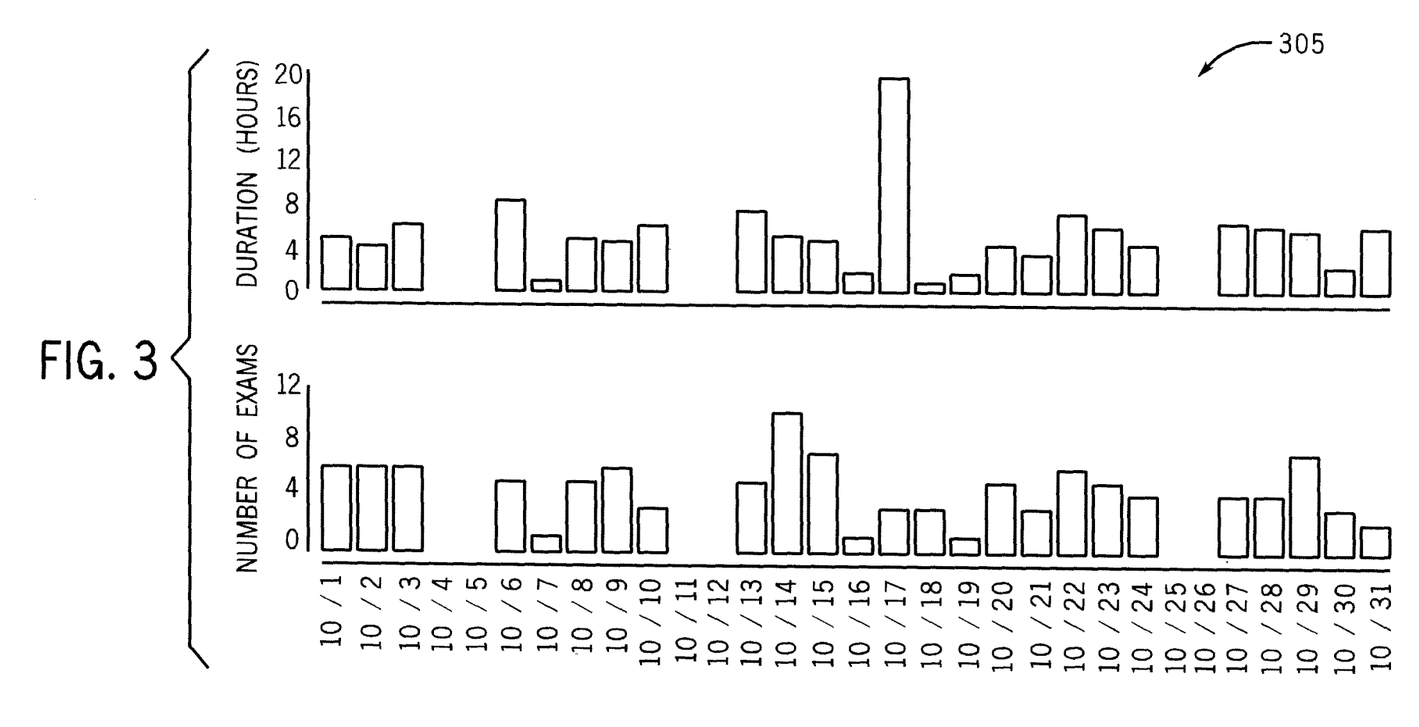
FIG. 3 shows an embodiment of an illustration of a number of examinations or image acquisitions or scans performed by the imaging system 130 and a tracked duration thereof over a period of time, generated by the system of FIG. 1.

Referring to FIG. 3, an example of the report 240 can include an illustration 305 (e.g., bar graph) of a number of examinations or image acquisitions or scans performed by the imaging system 130 and a tracked duration thereof over a period of time (e.g., per user input or standard periodic reporting period (e.g., monthly)).

Figure 4:
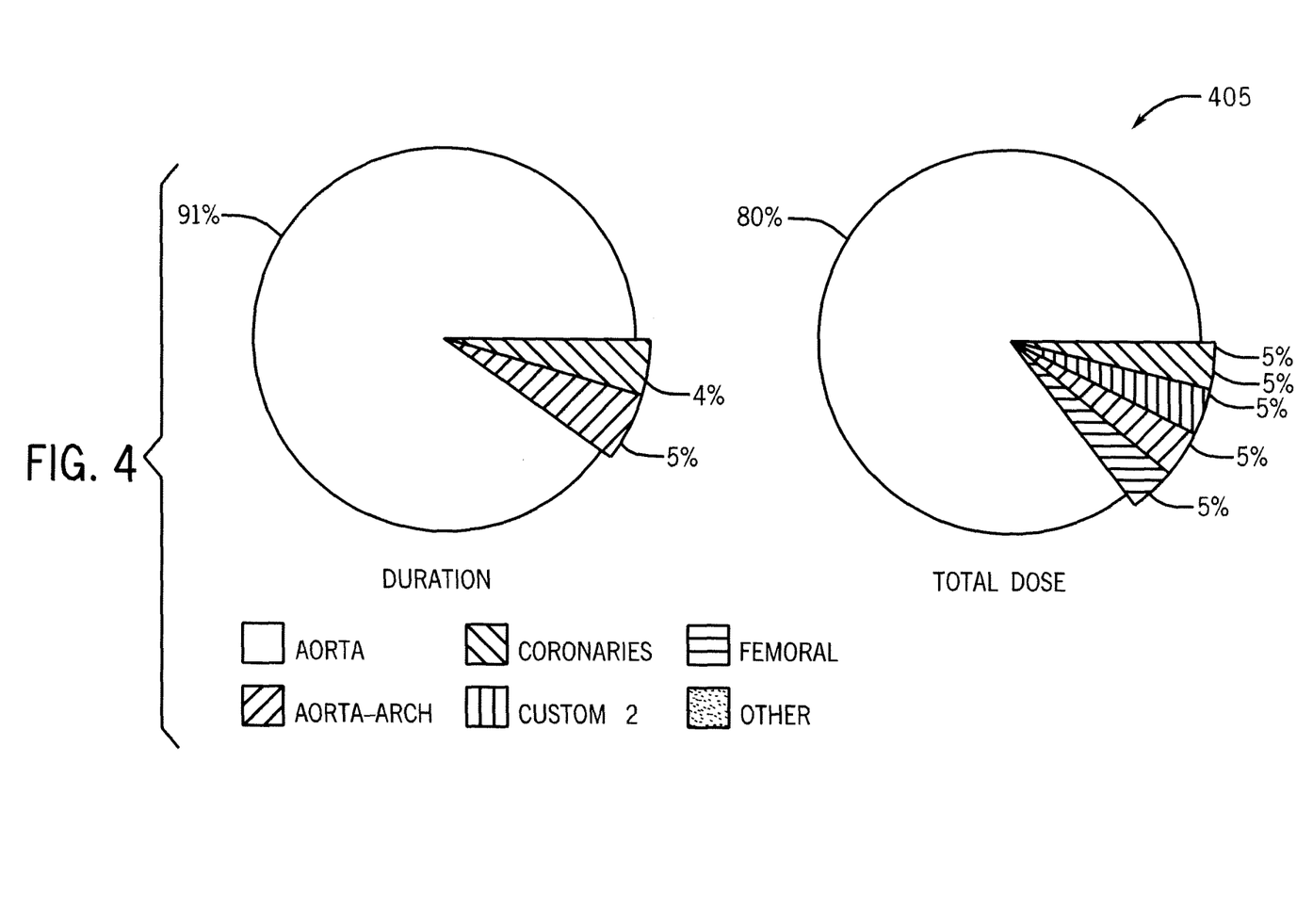
FIG. 4 shows an embodiment of an illustration of a duration per protocol employing direction of ionizing radiation to the exposed subject and comparison of performance of different protocols relative to one another, generated by the system of FIG. 1.

Referring to FIG. 4, an example of the report 240 can include an illustration 405 (e.g., graphic pie chart) indicative of the duration of the protocol employing direction of ionizing radiation and/or total dose directed to the exposed subject per the distribution of protocols (e.g., imaging of aorta, aorta-arch, coronaries, femoral, other) exposed to the ionizing radiation). The illustrated FIG. 4 can illustrate a frequency of performance of different protocols relative to one another and an associated distribution of radiation dose to the exposed subject 105.

Figure 5:
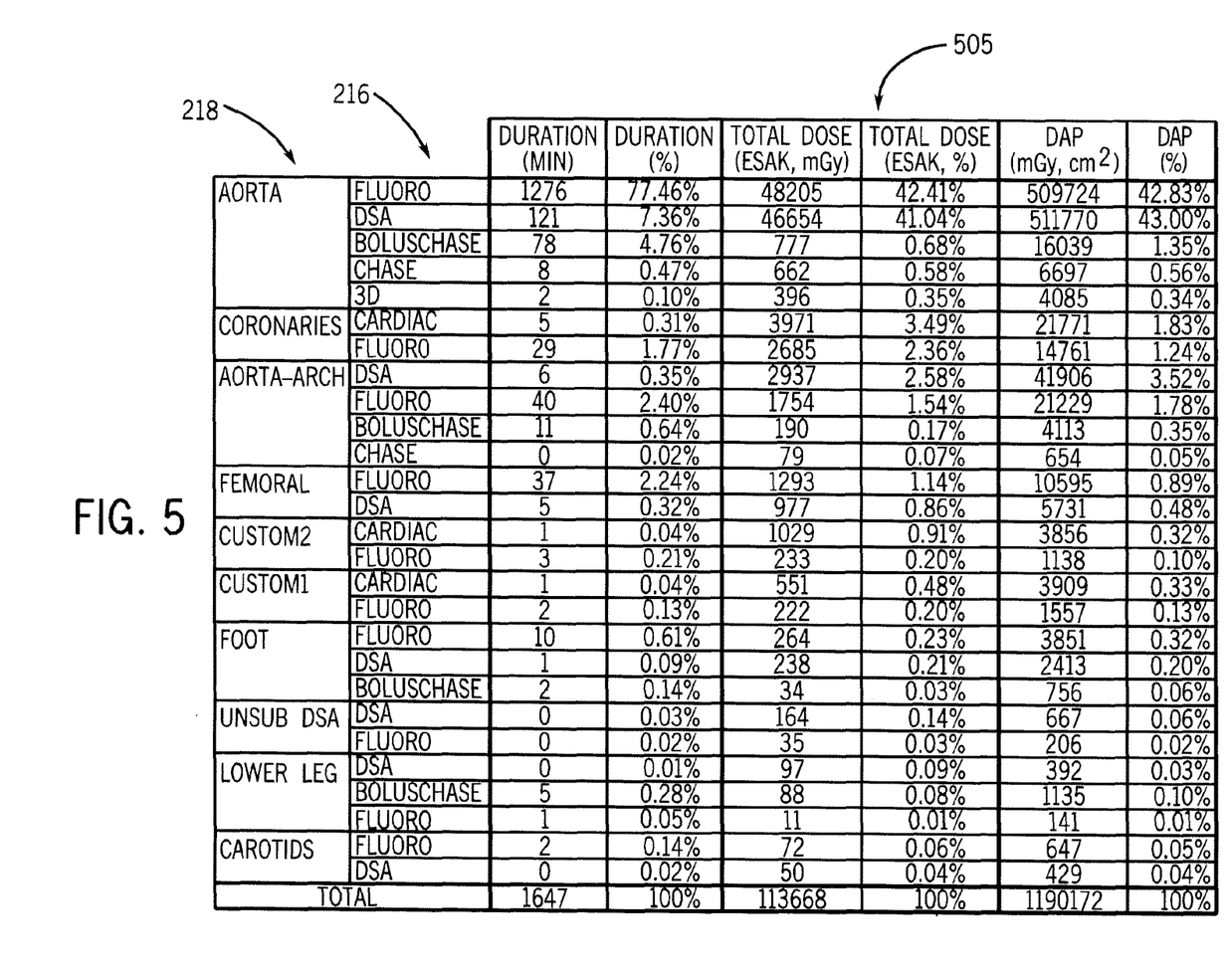
FIG. 5 shows an embodiment of an illustration of measured radiation dose directed to the exposed subject and cumulative percentile (%) for comparison relative to type of protocol and image acquisition mode, generated by the system of FIG. 1.

Referring to FIG. 5, an example of the report 240 can include an illustration 505 of measured radiation dose (e.g., cumulative dose, duration of exposure to radiation, DAP (product of dose multiplied by area of radiation beam) reported in Gy/cm^2) directed to the exposed subject and cumulative percentile (%) for comparison relative to type of protocol (aorta, coronaries, imaging of aorta-arch, femoral, foot, lower leg, carotids, etc.), as well as relative to image acquisition mode (e.g., cardiac, fluoroscopy, digital subtraction angiography (DSA), etc.).

Figure 6:
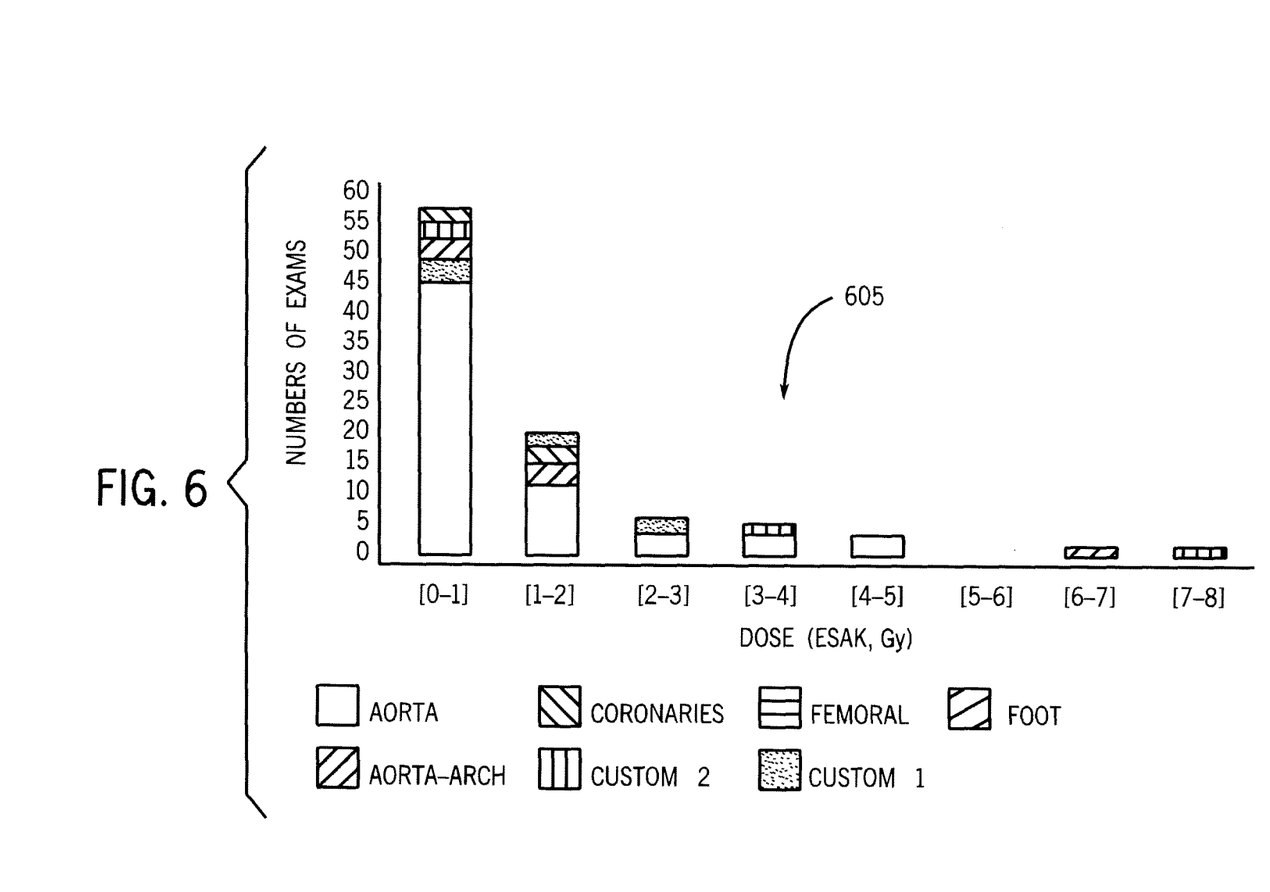
FIG. 6 shows an embodiment of an illustration of a distribution of a number of events that exceed a certain grouping or threshold range of radiation dose directed to the exposed subject, generated by the system of FIG. 1.

Referring to FIG. 6, an example of the report 240 can include an illustration 605 (e.g., bar graph) of a distribution of a number of events (e.g., exams, radiation therapy treatments, etc.) that exceed a certain grouping or threshold range of radiation dose (e.g., grouped in 1 Gy dose range increments) directed to the exposed subject 105. An embodiment of the illustration can include a measure of number of image acquisitions (e.g., scans, exams) where the measured radiation dose exceeded the radiation dose threshold, as defined to the right relative to a graphic representation 610 of the threshold (e.g., dotted line).

Figure 7:
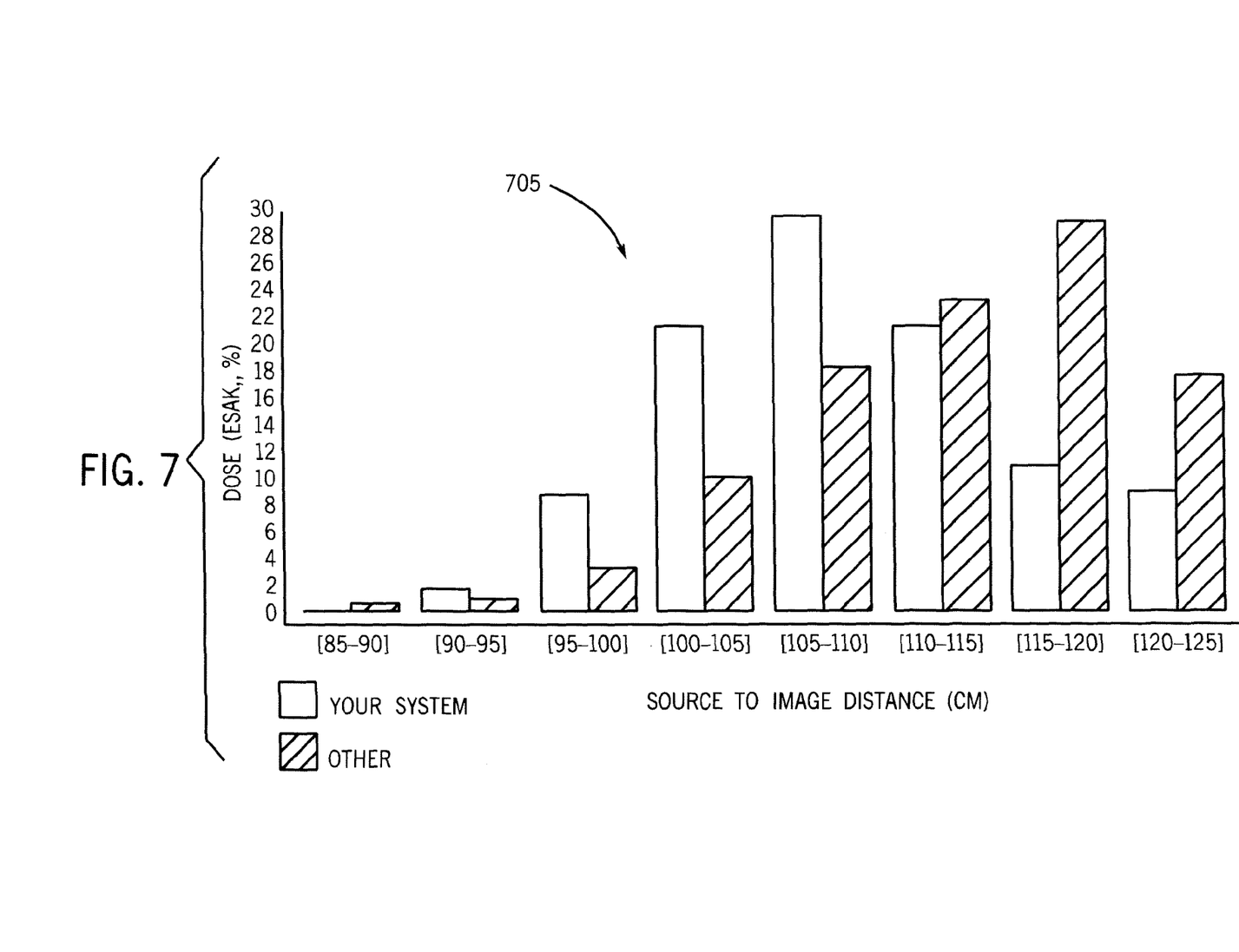
FIG. 7 shows an embodiment of an illustration of a distribution of radiation dose directed to the exposed subject relative to variance in the source to image distance (SID) of the ionizing radiation system, generated by the system of FIG. 1.

Referring to FIG. 7, an example of the report 240 can include an illustration 705 (e.g., bar graph) of a distribution of radiation dose directed to the exposed subject 105 relative to variance in the source to image distance (SID) for the individual system 130. This illustration relative to the individual system 130 can include a comparison relative to analogous distribution of radiation dose versus variance in SID for a population of other image acquisition systems 170 of similar type, or employed in similar protocol of mode of image acquisition. The variance in SID (e.g., in centimeters) can be illustrated in groupings along the horizontal axis, and the vertical bar graphic illustration can represent the percentage of total monthly cumulative radiation dose directed (e.g., ESAK, %). From this illustration, the user of the imaging system 105 can understand a potential reduction in radiation dose with change in the SID.

Figure 8:
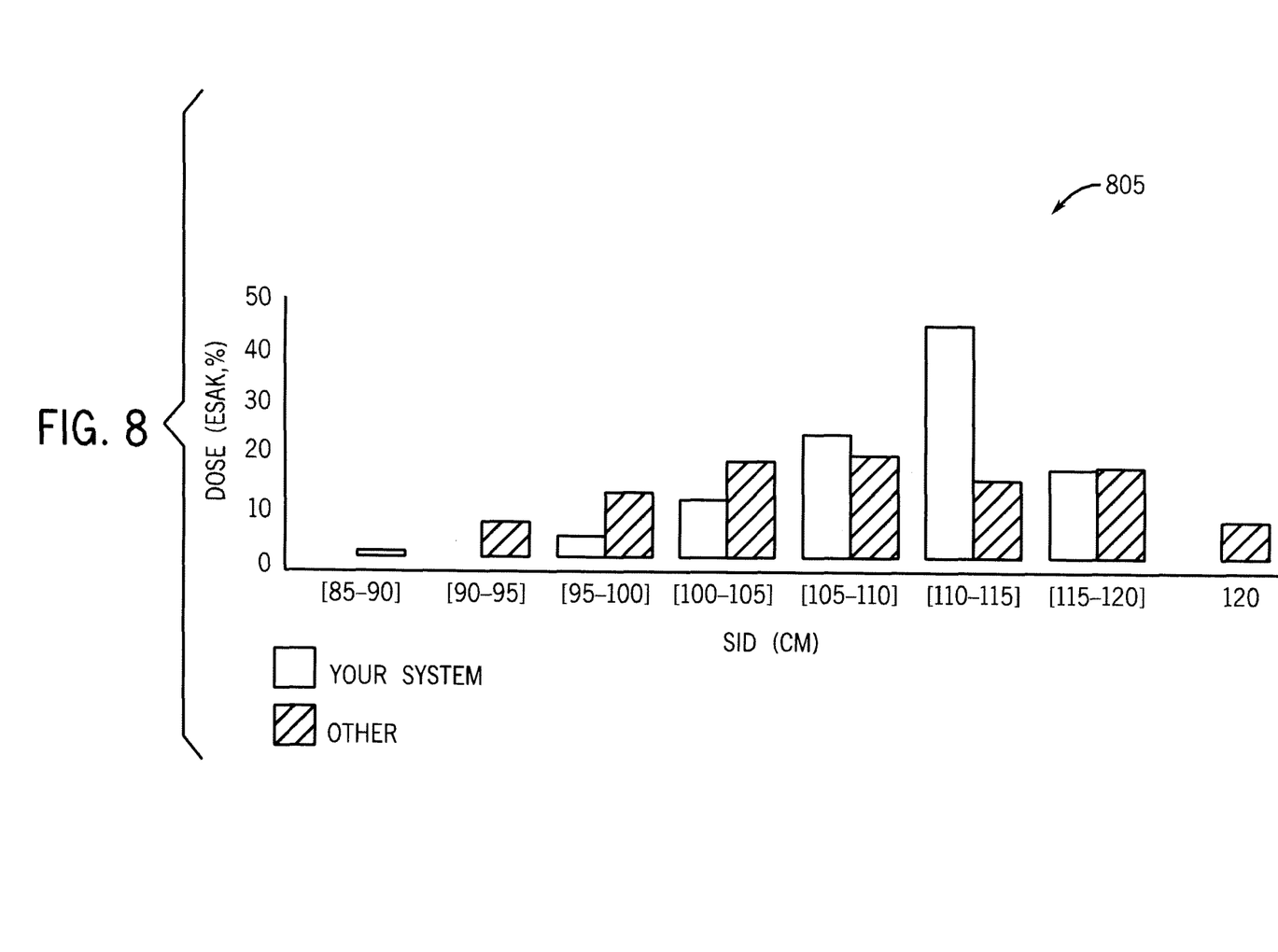
FIG. 8 shows an embodiment of an illustration of a distribution of SID for an individual imaging system relative to a benchmark defined by data acquired from one or more similar types of imaging systems, similar protocols of image acquisition, or similar modes of image acquisition or combination thereof, generated by the system of FIG. 1.

Referring to FIG. 8, an example of the report 240 can include an illustration 805 (e.g., bar graph) of a distribution of SID for the individual imaging system 130 relative to a benchmark defined by data acquired from one or more similar types of imaging systems 170, similar protocols of image acquisition, or similar modes of image acquisition or combination thereof. The illustrated example shows the SID in groupings (e.g., range of centimeters) along the horizontal axis relative to a vertical bar graphic illustration of cumulative radiation dose for each SID grouping, and further split out or illustrated relative to mode of image acquisition (e.g., fluoroscopy, cardiac, etc.).

Figure 9:
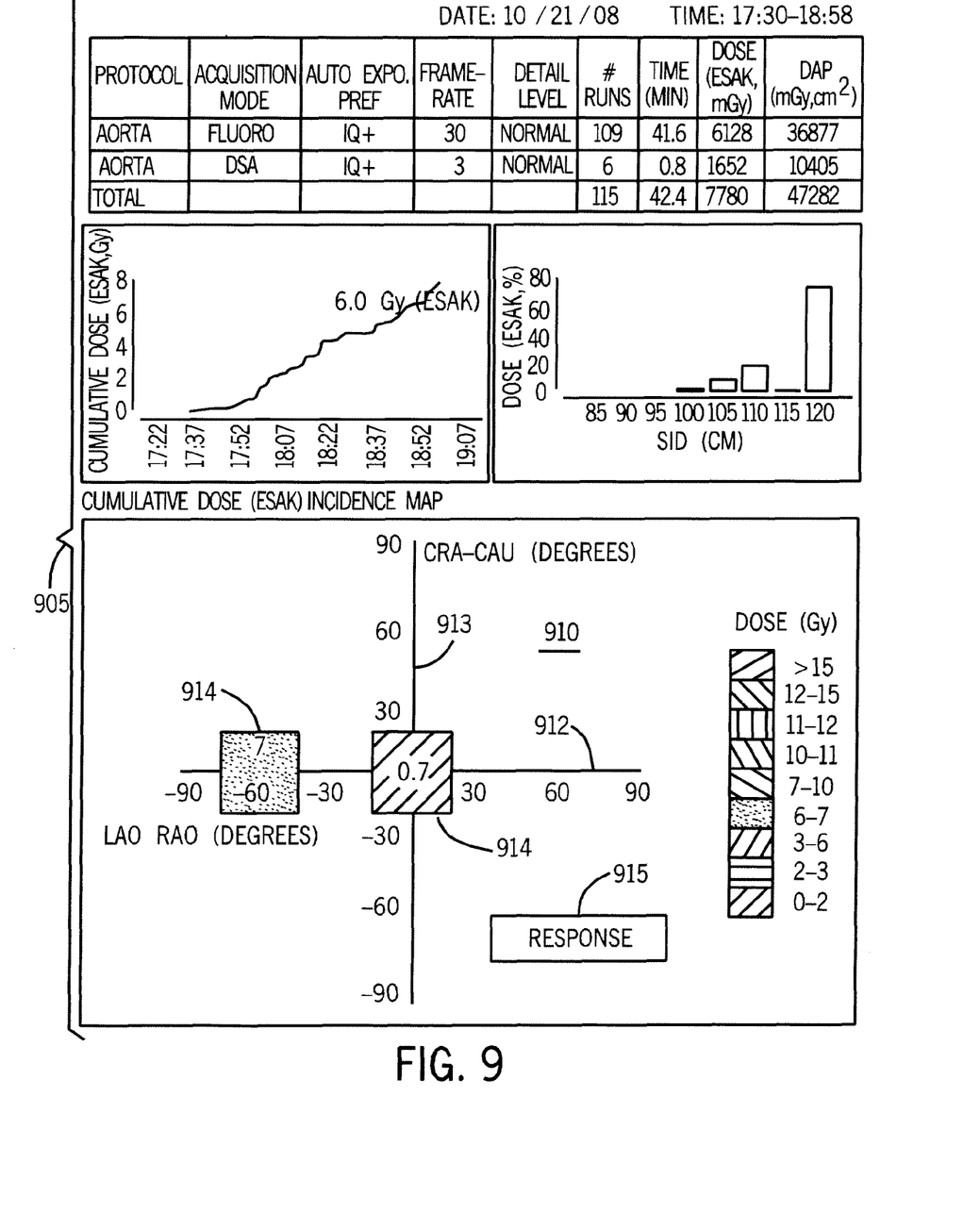
FIG. 9 shows an embodiment of an illustration of an incident map that correlates dose level and location of the direction of an above-threshold radiation directed to an exposed subject relative to the geometry of the gantry in support of the ionizing radiation source, generated by the system of FIG. 1.

Referring to FIG. 9, an example of the report 240 can include an illustration 905 of an image acquisition scan or examination or therapy status information where a measure of the radiation dose (e.g., cumulative radiation dose) directed to an exposed subject exceeds the radiation dose threshold. The example illustration in FIG. 9 can include detailed status information associated with the examination, acquisition scan, or therapy session where the radiation dose threshold was exceeded, including the following: date/time stamp of examination, protocol (e.g., coronaries, etc.), type of acquisition mode (e.g., fluoroscopy), auto exposure preference, frame rate, image acquisition detail level, number of runs or scans in examination, total duration of examination, and cumulative radiation dose (e.g., ESAK, Gy) and DAP (mGy/cm^2) directed to the exposed subject 105.

The example illustration 905 in FIG. 9 can further include a calculation of equivalent patient thickness (EPT) (i.e., a thickness of acrylic plastic or the like (PMMA) that produces the same average radiation attenuation as the patient of interest under the given situation that can represent an indication of the difficulty in penetrating the patient with a sufficient number of ionizing radiation to form a useful image) that can be employed by the user to manage imaging dose efficiency optimization, and to automatically set parameters of the imaging system when transitioning between imaging modes without acquiring test exposures. The example illustration 905 in FIG. 9 can further includes an illustration of the measure of cumulative radiation dose directed to the exposed subject 105 over time, and the point in time of the examination when the radiation dose exceeded the threshold for the examination of interest. The example illustration 905 in FIG. 9 can also include a graphic representation (e.g., bar graph) of the SID or grouping thereof relative to the measure of radiation dose directed to the exposed subject 105 during the examination of interest where the threshold was exceeded. The example illustration 905 can also show how changes in the SID can affect the radiation dose directed to the exposed subject 105.

The example illustration 905 in FIG. 9 can further include an embodiment of a cumulative dose incident map 910 associated with the examination of interest where the radiation dose exceeded the threshold. The embodiment of the cumulative dose incident map 910 can include an illustration of the measure of cumulative radiation dose (ESAK) directed to the exposed subject during the examination relative to the tracked position or angulation of the radiation source 125 and/or detector 140 of the imaging system 130. The tracked position (e.g. angulation) of the radiation source 125 and/or detector 140 can be correlated to the tracked position (e.g., angulation) of the gantry 128 in support of the radiation source 125 or detector 140. The cumulative dose incident map 910 can include a horizontal axis 912 to represent varied positions of the gantry 128 with respect to left/right anterior oblique (LAO/RAO) position of the exposed subject 105, and a vertical axis 913 that can represent cranial/caudal positions of the gantry 128. The cumulative dose incident map 910 can also include a graphic representation 914 of the distribution of the radiation dose (e.g., ESAK) to the exposed subject 105 relative to the position (e.g., angulation) of the gantry 128 (e.g., thirty degree increments) or the axes 912, 913. Thereby, the cumulative dose incident map 910 can illustrate the measure of the radiation dose as well as how radiation dose was directed to the exposed subject 105.

Step 235 can further include identifying a proposed response or action 915 (See FIG. 9) to reduce the radiation dose to the exposed subject 105, dependent in response to detecting the radiation dose exceeding the threshold according to the status information of the imaging system 130 in directing the ionizing radiation to the exposed subject 105. The proposed response or action 915 can be generated dependent on acquired data of responses or actions and tracked reduction in radiation dose to the exposed subject 105 as tracked or measured by one or more other users or other imaging systems 170, different from the imaging system 130 of interest. Although the proposed response or actions 915 is illustrated in FIG. 9, the proposed response or action 915 can be part of any of the other illustrated FIGS. 3-8 or independent thereof.

The subject matter herein describes the system 100 and method 200 to manage direction of the ionizing radiation 130 toward the exposed subject 105. The method 200 includes the steps of receiving a request 208 from a customer to establish an internet or broadband connection 118 to communicate between the remote office 112 and the system 130 directing the ionizing radiation toward the exposed subject 105; automatically communicating a status information and individual dose data associated with an event where direction of ionizing radiation 135 that exceeds a threshold; automatically creating and communicating the report 240 to the user display 245 of the customer, the report 240 including an indication of the event where direction of ionizing radiation 135 exceeds the threshold and a comparison of the individual radiation dose data and an individual status operation of the ionizing radiation system 120 at time of the event relative to a benchmark defined by radiation dose data and status information acquired from a population of other systems 170 that direct ionizing radiation and communicate data to the remote office 112. The system 120 that directs the ionizing radiation can be a radiological imaging system 130, and the comparison can include a number of acquired images of the individual radiological imaging system 130 relative to a number of acquired images of at least one of the population of other radiological imaging systems 170.

The method 200 can include calculating the individual radiation dose data for at least one acquired image exceeds the threshold triggers the step of automatically communicating the acquired status information and individual dose data from the remote office 112 to the user display 245 of the customer. The method 200 can further include comparing data from the individual ionizing radiation system 120 can be relative to data of the one or more of the population of ionizing radiation systems 170 associated each of the following: a duration of a protocol employing the direction of ionizing radiation per a distribution of types of protocols, a frequency of performance of different protocols relative to one another and an associated distribution of radiation dose to the exposed subject 105, the radiation dose, duration of exposure to the ionizing radiation 135, product of the radiation dose multiplied by an area of the beam of ionizing radiation 135 directed to the exposed subject 105, and distribution of radiation dose relative to a type of image acquisition mode.

The method 200 can further include comparison of data from the individual ionizing radiation system 120 relative to data of the one or more of the population of ionizing radiation systems 170 associated each of the following: a distribution of a number of events with the individual system 120 where the radiation dose directed to the exposed subject exceeds the threshold radiation dose, a distribution of radiation dose directed to the exposed subject 105 relative to a variance in the source to image distance (SID), a distribution of SID for the individual system 120 relative to a benchmark defined by data acquired from one or more similar types of other systems 170 performing similar protocols or modes of ionizing radiation operation, an auto exposure preference, a frame rate of image acquisition, a calculated value of an equivalent exposed subject thickness that produces the same average radiation attenuation, and a point in time of the examination when the radiation dose exceeded the radiation dose threshold.

The method 200 can further comprise the steps of calculating a individual trend in a history of the individual radiation dose acquired from the individual radiological imaging system 130; and comparing the individual trend relative to a population trend calculated from a history of the population radiation dose data acquired from the population of other radiological imaging systems 170 for a selected time frame as received from the customer.

Embodiments of the report 240 can include an illustration of a cumulative dose incident map 910 associated with the examination of interest where the radiation dose exceeded the threshold. The embodiment of the cumulative dose incident map 910 can include the measure of cumulative radiation dose (ESAK) directed o the exposed subject 105 during the examination relative to the tracked position or angulation of the radiation source 125 and/or detector 140 of the imaging system 130, the tracked position or angulation of the radiation source 125 and/or detector 140 can be correlated to the tracked position or angulation of the gantry 128 in support of the radiation source 125 or detector 140. Embodiments of the report 230 can includes a cumulative dose incident map 910 that comprises a graphic illustration of a horizontal axis 912 to represent varied positions of a gantry in support of a source of the ionizing radiation with respect to a left/right anterior oblique (LAO/RAO) position of the exposed subject, a graphic illustration of a vertical axis 913 that represents a cranial or caudal position of the gantry 128, and a graphic representation 914 of a distribution of radiation dose relative to the horizontal and vertical axes 912 and 913.

The subject matter herein also describes the system 100 can include a computer readable medium 155 including a plurality of program instructions for execution by a processor 150 to perform the steps of receiving the request 208 from the customer to establish the internet or broadband connection 118 to communicate between the remote office 112 and the system 120 directing the ionizing radiation toward the exposed subject 105; automatically communicating a status information and individual dose data associated with an event where direction of ionizing radiation 135 that exceeds a threshold; automatically creating and communicating a report via the internet connection to the customer, the report including an indication of the event where direction of ionizing radiation exceeds the threshold and a comparison of the individual radiation dose data and an individual status operation of system at time of the event relative to a benchmark defined by radiation dose data and status information acquired from a population of other systems that direct ionizing radiation and communicate data to the remote office. The program instructions of the computer readable medium can instruct the processor 150 upon calculating the individual radiation dose data for at least one acquired image that exceeds the threshold, then to trigger the step of automatically communicating the acquired status information and individual dose data from the remote office 112 to the user display 245 of the customer.

The program instructions of the computer readable medium can further instruct the processor 150 to perform comparison of data from the individual ionizing radiation system 120 relative to data of the one or more of the population of ionizing radiation systems 170 further associated each of the following: a duration of a protocol employing the direction of ionizing radiation 135 per a distribution of types of protocols 216, a frequency of performance of different protocols 216 relative to one another and an associated distribution of radiation dose directed to the exposed subject 105, the radiation dose, duration of exposure to the ionizing radiation 135, a product of the radiation dose multiplied by an area of the beam of ionizing radiation 135 directed to the exposed subject 105, and a distribution of radiation dose relative to a type of image acquisition mode 216.

Another embodiment of the program instructions of the computer readable medium can further instruct the processor 150 to perform comparison of data from the individual ionizing radiation system 120 relative to data of the one or more of the population of ionizing radiation systems 170 further associated each of the following: a distribution of a number of events with the individual system 130 where the radiation dose directed to the exposed subject 105 exceeds the threshold radiation dose, a distribution of radiation dose directed to the exposed subject 105 relative to a variance in the source to image distance (SID) 222, a distribution of SID for the individual system 120 relative to a benchmark defined by data acquired from one or more similar types of other systems 170 performing similar protocols 216 or modes of ionizing radiation operation, an auto exposure preference, a frame rate of image acquisition, a calculated value of an equivalent exposed subject thickness that produces the same average radiation attenuation, and a point in time of the examination when the radiation dose exceeded the radiation dose threshold.

Embodiments of the computer readable medium can further comprise program instructions to instruct the processor 150 to perform the steps of calculating a individual trend in a history of the individual radiation dose acquired from the individual radiological imaging system 170; and comparing the individual trend relative to a population trend calculated from a history of the population radiation dose data acquired from the population of other radiological imaging systems 170 for a selected time frame (e.g., received from the customer).

The computer readable medium can also include program instructions to instruct the processor 150 to generate the report 240 to include the cumulative dose map 910 associated with the examination of interest where the radiation dose exceeded the threshold. The embodiment of the cumulative dose incident map 910 can include an illustration of the measure of cumulative radiation dose (ESAK) directed to the exposed subject during the examination relative to the tracked position or angulation of the radiation source 125 and/or detector 140 of the imaging system 130, the tracked position or angulation of the radiation source 125 and/or detector 140 can be correlated to the tracked position or angulation of the gantry 128 in support of the radiation source 125 or detector 140.

Embodiment of the program instructions can also instruct the processor 150 to generate the report 240 to further include the cumulative dose incident map 910 that comprises a graphic illustration 912 of a horizontal axis to represent varied positions of the gantry 128 in support of the source 125 of the ionizing radiation with respect to a left/right anterior oblique (LAO/RAO) position of the exposed subject 105, a graphic illustration 913 of a vertical axis that represents a cranial or caudal position of the gantry 128, and a graphic representation 914 of a distribution of radiation dose directed to the exposed subject 105 relative to the horizontal and vertical axes 912, 913 of the map 910.

A technical effect of the subject matter described above includes providing the system 100 and method 200 to address concerns associated with use of ionizing radiation, and the need for access to data or increased knowledge to manage directing radiation dose to the exposed subject (e.g., patient) for different applications (e.g., fluoroscopic imaging, x-ray imaging, CT imaging of various exposed areas (e.g., chest, arms, legs, etc.) of an exposed subject). This improved access to data can benefit the establishment of standard operating procedures and protocols in the use of ionizing radiation to perform various tasks, as well as benefit the measurement and evaluation of an impact of each procedure's protocol in the likelihood for burn or other late effects associated with exposure to ionizing radiation relative to the characteristics of exposed subjects 105.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A computer-implemented method to manage direction of an ionizing radiation toward an exposed subject, comprising using a processor-based system at a remote office for:
   executing code on the processor-based system to establish an internet connection to communicate with a system directing the ionizing radiation toward the exposed subject;
   executing code on the processor-based system to communicate a status information and individual dose data associated with an event and where direction of ionizing radiation exceeds a threshold;
   executing code on the processor-based system to create and communicate a report via the internet connection to a display of a user workstation, the report including an indication of the event where direction of ionizing radiation exceeds the threshold and a comparison of the individual radiation dose data and an individual status operation of the system at time of the event relative to a benchmark defined by radiation dose data and status information acquired from a population of other systems that direct ionizing radiation, wherein the report also includes a graphical representation, comprising:
      a cumulative dose incident map depicting a measure of cumulative radiation dose directed to the exposed subject and having at least two axes that correspond to a geometry of the system directing the ionizing radiation toward the subject, wherein the at least two axes of the cumulative dose incident map comprise a graphic illustration of a horizontal axis to represent varied positions of a gantry in support of a source of the ionizing radiation with respect to a left/right anterior oblique (LAO/RAO) position of the exposed subject and a graphic illustration of a vertical axis that represents a cranial or caudal position of the gantry; and
      a graphic representation of a distribution of radiation dose to the exposed subject relative to the at least two axes.

2. The computer-implemented method of claim 1, wherein the system that directs the ionizing radiation is a radiological imaging system, and wherein the comparison includes a number of acquired images of the individual radiological imaging system relative to a number of acquired images of at least one of the population of other radiological imaging systems.

3. The computer-implemented method of claim 2, wherein calculating the individual radiation dose data for at least one acquired image that exceeds the threshold triggers the step of automatically communicating the acquired status information and individual dose data from the remote office to the customer.

4. The computer-implemented method of claim 1, wherein the comparison of data from the individual ionizing radiation system relative to data of the one or more of the population of ionizing radiation systems further is associated with each of the following: a duration of a protocol employing the direction of ionizing radiation per a distribution of types of protocols, a frequency of performance of different protocols relative to one another and an associated distribution of radiation dose directed to the exposed subject, the radiation dose, duration of exposure to the ionizing radiation, product of the radiation dose multiplied by an area of the beam of ionizing radiation directed to the exposed subject, and distribution of radiation dose relative to a type of image acquisition mode.

5. The computer-implemented method of claim 1, wherein the comparison of data from the individual ionizing radiation system relative to data of the one or more of the population of ionizing radiation systems further is associated each of the following: a distribution of a number of events with the individual system where the radiation dose directed to the exposed subject exceeds the threshold radiation dose, a distribution of radiation dose directed to the exposed subject relative to a variance in the source to image distance (SID), a distribution of SID for the individual system relative to a benchmark defined by data acquired from one or more similar types of other systems performing similar protocols or modes of ionizing radiation operation, an auto exposure preference, a frame rate of image acquisition, a calculated value of an equivalent exposed subject thickness that produces the same average radiation attenuation, and a point in time of the examination when the radiation dose exceeded the radiation dose threshold.

6. The computer-implemented method of claim 1, further comprising the steps of: calculating an individual trend in a history of the individual radiation dose acquired from the individual radiological imaging system; and comparing the individual trend relative to a population trend calculated from a history of the population radiation dose data acquired from the population of other radiological imaging systems for a selected time frame as received from the user.

7. The computer-implemented method of claim 1, wherein the cumulative dose incident map is associated with the examination of interest where the radiation dose exceeded the threshold, and wherein the cumulative dose incident map depicts the measure of cumulative radiation dose directed to the exposed subject during the examination relative to the tracked position or angulation of the radiation source and/or detector of the imaging system, wherein the tracked position or angulation of the radiation source and/or detector can be correlated to the tracked position or angulation of the gantry in support of the radiation source or detector.

8. The method of claim 1, wherein the report further comprises a proposed response to reduce the radiation dose to the exposed subject.

9. A non-transitory computer readable medium including a plurality of program instructions for execution by a processor to perform the steps of:
- receiving a request from a customer to establish an internet connection to communicate between a remote office and a system directing the ionizing radiation toward the exposed subject;
- automatically communicating a status information and individual dose data associated with an event where direction of ionizing radiation exceeds a threshold;
- automatically creating and communicating a report via the internet connection to the customer, the report including an indication of the event where direction of ionizing radiation exceeds the threshold and a comparison of the individual radiation dose data and an individual status operation of the system at time of the event relative to a benchmark defined by radiation dose data and status information acquired from a population of other systems that direct ionizing radiation, wherein the report also includes a graphical representation, comprising:
  - a cumulative dose incident map depicting a measure of cumulative radiation dose directed to the exposed subject and having at least two axes that correspond to a geometry of the system directing the ionizing radiation toward the subject, wherein the at least two axes of the cumulative dose incident map comprise a graphic illustration of a horizontal axis to represent varied positions of a gantry in support of a source of the ionizing radiation with respect to a left/right anterior oblique (LAO/RAO) position of the exposed subject and a graphic illustration of a vertical axis that represents a cranial or caudal position of the gantry; and
  - a graphic representation of a distribution of radiation dose to the exposed subject relative to the at least two axes.

10. The non-transitory computer readable medium of claim 9, wherein calculating the individual radiation dose data for at least one acquired image that exceeds the threshold triggers the step of automatically communicating the acquired status information and individual dose data from the remote office to the customer.

11. The computer non-transitory readable medium of claim 9, wherein the comparison of data from the individual ionizing radiation system relative to data of the one or more of the population of ionizing radiation systems further is associated with each of the following: a duration of a protocol employing the direction of ionizing radiation per a distribution of types of protocols, a frequency of performance of different protocols relative to one another and an associated distribution of radiation dose directed to the exposed subject, the radiation dose, duration of exposure to the ionizing radiation, product of the radiation dose multiplied by an area of the beam of ionizing radiation directed to the exposed subject, and distribution of radiation dose relative to a type of image acquisition mode.

12. The non-transitory computer readable medium of claim 9, wherein the comparison of data from the individual ionizing radiation system relative to data of the one or more of the population of ionizing radiation systems further is associated each of the following: a distribution of a number of events with the individual system where the radiation dose directed to the exposed subject exceeds the threshold radiation dose, a distribution of radiation dose directed to the exposed subject relative to a variance in the source to image distance (SID), a distribution of SID for the individual system relative to a benchmark defined by data acquired from one or more similar types of other systems performing similar protocols or modes of ionizing radiation operation, an auto exposure preference, a frame rate of image acquisition, a calculated value of an equivalent exposed subject thickness that produces the same average radiation attenuation, and a point in time of the examination when the radiation dose exceeded the radiation dose threshold.

13. The non-transitory computer readable medium of claim 9, further comprising the steps of: calculating an individual trend in a history of the individual radiation dose acquired from the individual radiological imaging system; and comparing the individual trend relative to a population trend calculated from a history of the population radiation dose data acquired from the population of other radiological imaging systems for a selected time frame as received from the user.

14. The non-transitory computer readable medium of claim 9, wherein the cumulative dose incident map is associated with the examination of interest where the radiation dose exceeded the threshold, and wherein the cumulative dose incident map depicts the measure of cumulative radiation dose directed to the exposed subject during the examination relative to the tracked position or angulation of the radiation source and/or detector of the imaging system, wherein the tracked position or angulation of the radiation source and/or detector can be correlated to the tracked position or angulation of the gantry in support of the radiation source or detector.

15. The non-transitory computer readable medium of claim 9, wherein the report further comprises a proposed response to reduce the radiation dose to the exposed subject.

* * * * *